US011154518B2

(12) United States Patent
Lu et al.

(10) Patent No.: US 11,154,518 B2
(45) Date of Patent: Oct. 26, 2021

(54) METHODS AND APPARATUS FOR TREATING A WOUND

(71) Applicants: Chang Gung Memorial Hospital, Linkou, Taoyuan (TW); Chang Gung University, Taoyuan (TW); National Cheng Kung University, Tainan (TW)

(72) Inventors: Chun-Wei Lu, Taoyuan (TW); Jong-Hwei Su Pang, Taoyuan (TW); Yu-Shien Ko, Taoyuan (TW); Wen-Hung Chung, Taoyuan (TW); Chao-Kai Hsu, Tainan (TW)

(73) Assignees: CHANG GUNG MEMORIAL HOSPITAL, LINKOU, Taoyuan (TW); CHANG GUNG UNIVERSITY, Taoyuan (TW); NATIONAL CHENG KUNG UNIVERSITY, Tainan (CN)

( * ) Notice: Subject to any disclaimer, the term of this patent is extended or adjusted under 35 U.S.C. 154(b) by 49 days.

(21) Appl. No.: 16/234,867

(22) Filed: Dec. 28, 2018

(65) Prior Publication Data
US 2020/0206164 A1 Jul. 2, 2020

(51) Int. Cl.
| | |
|---|---|
| *A61L 15/00* | (2006.01) |
| *A61K 31/138* | (2006.01) |
| *A61P 17/02* | (2006.01) |
| *A61K 9/70* | (2006.01) |
| *A61K 45/06* | (2006.01) |

(52) U.S. Cl.
CPC .......... *A61K 31/138* (2013.01); *A61K 9/7007* (2013.01); *A61K 45/06* (2013.01); *A61P 17/02* (2018.01)

(58) Field of Classification Search
CPC .... A61K 9/7007; A61K 31/138; A61K 45/06; A61P 17/02
See application file for complete search history.

(56) References Cited

U.S. PATENT DOCUMENTS

| | | | | |
|---|---|---|---|---|
| 2010/0273889 | A1* | 10/2010 | Leaute-Labreze | ...... A61P 17/00 514/652 |
| 2011/0021526 | A1* | 1/2011 | Deshpande | ............ A61K 31/00 514/236.2 |
| 2016/0175485 | A1 | 6/2016 | Isseroff et al. | |

OTHER PUBLICATIONS

Yen et al. J Am Acad Dermatol. 2018; 78(6): e143-e144. (Epub Jan. 18, 2018). (Year: 2018).*
Hillson. Nails in Diabetes. Practical Diabetes [online]; 2017; downloaded from <URL https://www.practicaldiabetes.com/article/nails-in-diabetes/ > on Aug. 18, 2020; 7 pages. (Year: 2017).*
Chi-Feng Yen et al., "Topical betaxolol for treating relapsing paronychia with pyogenic granuloma-like lesions induced by epidermal growth factor receptor inhibitors," J Am Acad Dermatol, Jun. 2018, pp. e143-e144.
Christine E. Pullar et al., "Beta2-Adrenergic receptor activation delays wound healing," The FASEB Journal, Jan. 2006, vol. 20, pp. 76-86.
Christine E. Pullar et al., "beta-Adrenergic receptor antagonists accelerate skin wound healing: evidence for a catecholamine synthesis network in the epidermis," J Biol Chem., Jul. 28, 2006, pp. 21,225-21,235, vol. 281, No. 30.
Ashlesha P. Pandit et al., "Nebivolol-Loaded Microsponge Gel for Healing of Diabetic Wound," AAPS PharmSciTech, Jun. 29, 2016.
Xavier Cubiro et al., "Topical Timolol for Paronychia and Pseudopyogenic Granuloma in Patients Treated With Epidermal Growth Factor Receptor Inhibitors and Capecitabine," JAMA Dermatology, E1-E2, Nov. 8, 2017.
Search Report for Corresponding Taiwan application No. 107147564, dated Sep. 9, 2019.

* cited by examiner

*Primary Examiner* — David Browe
(74) *Attorney, Agent, or Firm* — Pilloff Passino & Cosenza LLP; Sean A. Passino; Rachel K. Pilloff

(57) ABSTRACT

Methods for treating a wound or promote wound healing are provided, comprising the step of administering a composition including an effective amount of β-1 adrenergic receptor antagonist to a subject in need thereof. Also provided is apparatus for wound healing, comprising a dressing and a composition including an effective amount of β-1 adrenergic receptor antagonist.

6 Claims, 5 Drawing Sheets
(5 of 5 Drawing Sheet(s) Filed in Color)

METHODS AND APPARATUS FOR TREATING A WOUND

BACKGROUND OF THE INVENTION

Wound healing, initiated by whatever aetiology, is a dynamic process encompassing a number of overlapping phases, including inflammation, epithelialization, angiogenesis and matrix deposition. During the epithelization phase, keratinocytes migrate into the wound bed to initiate re-epithelization, necessary for wound closure and restoration of skin integrity. Keratinocytes solely express β2-adrenergic receptors and the activation of β2-adrenergic receptors delays wound healing (C E Pullar et al., Beta2-adrenergic receptor activations delays wound healing FASEB J. 2006 January; 20(1):76-86). Additional research demonstrates β2-adrenergic antagonists accelerate skin wound re-epithelizliation, due to β2-adrenergic blockade to prevent the binding of endogenously synthesized epinephrine (CE Pullar et al., Beta-adrenergic receptor antagonists accelerate skin wound healing: evidence for a catecholamine synthesis network in the epidermis, J Biol Chem. 2006 Jul. 28; 281(30):21225-35. Epub 2006 May 19).

Normally, the wound healing processes lead to a mature wound and a certain degree of scar formation. Although a variety of factors affect wound healing, including age, nutrition, obesity, repetitive trauma, skin moisture, concurrent illness (e.g., diabetes) and medication, most wounds heal along a prescribed course without difficulty.

The science of wound repair and care has progressed significantly since the discovery of the first growth factor (epidermal growth factor) in 1962 and the moist wound concept for healing. Despite these advanced wound care treatments, a minority of wounds will not respond to the current wound management.

There is an unmet need for the management of wound to promote wound healing. The present invention addresses these and other needs.

BRIEF SUMMARY OF THE INVENTION

In one embodiment, the present invention discloses methods for treating a wound or promote wound healing, comprising the step of administering a composition comprising an effective amount of a β-1 adrenergic receptor antagonist to a patient in need thereof.

The present invention also discloses apparatus for treating a wound or promote wound healing, comprising (a) a dressing; and (b) a composition comprising an effective amount of β-1 adrenergic receptor antagonist.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

The patent contains at least one drawing executed in color. Copies of this patent with color drawings will be provided by the Office upon request and payment of the necessary fee.

Illustrative embodiments of the present invention are described in detail below with reference to the following Figures.

DETAILED DESCRIPTION OF THE INVENTION

Figure 1A:
FIG. 1A and FIG. 1B are photo images of a patient with relapsing severe paronychia and pyogenic granuloma-like lesions of the left thumb before (FIG. 1A) and after 4 weeks of topical betaxolol treatment (FIG. 1B).

As used herein, the articles "a" and "an" refer to one or more than one (i.e., at least one) of the grammatical object of the article.

The term "subject" and "patient" may be used interchangeably and refer to a mammal diagnosed with a wound or suspected of having a wound. Subjects include primate, and more preferably, a human.

An "effective amount" of an antagonist refers to an amount of the antagonist that produces a desirable effect, e.g., increases the rate of wound healing by at least 1% compared to an untreated subject.

As used herein, the term "treating" refers to both therapeutic treatment and prophylactic or preventative measures. Those in need of treatment include those already with a wound or related disorder as well as those prone to having a wound or related disorder or those in which the wound is to be prevented.

All numbers herein may be understood as modified by "about." As used herein, the term "about" is meant to encompass variations of ±10%.

Methods for Wound Healing

The present invention is directed to methods of treating a wound or promote wound healing, comprising the step of administering a composition comprising an effective amount of a β-1 adrenergic receptor antagonist to the patient in need thereof.

As used herein, a "wound" is any disruption, from whatever cause, of a subject's internal or external body structure (e.g., epithelial tissue) including but not limited to traumatic injuries such as mechanical (i.e. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (e.g., paronychia caused by chemotherapy or target therapy, ulcers caused by diabetic neuropathy or venous stasis). Non limiting examples of wound include paronychia, acute ulcer, ulcer, surgical wound dehiscence, burn, laceration, incision or abrasion. As used herein, target therapy includes medications which inhibit the growth of cancer cells by interfering with specific targeted molecules needed for carcinogenesis and cancer growth, rather than by simply interfering with rapidly dividing cells (e.g., conventional chemotherapy), such as kinase inhibitor, angiogenesis inhibitor, epidermal growth factor receptor (EGFR) inhibitor, HER2/neu receptor or the combination thereof.

In some embodiments, the wound is a chronic wound. In an exemplary embodiment, chronic wound may refer to a wound that is characterized at least in part by one or more of 1) a chronic self-perpetuating state of wound inflammation, 2) a deficient and defective wound ECM, 3) poorly responding (senescent) wound cells especially fibroblasts, limiting ECM production, and 4) failure of re-epithelialization due in part to lack of the necessary ECM orchestration and lack of scaffold for migration. Non limiting examples of chronic wounds include venous ulcers, arterial ulcers, pressure ulcers, vasculitic ulcers, and diabetic ulcers.

In some embodiments, the wound is characterized in whole or in part by delayed or incomplete wound healing. In an exemplary embodiment, delayed or incomplete wound healing may include a wound that is characterized at least in part by one or more of the following: 1) a prolonged inflammatory phase, 2) a slow forming extracellular matrix (ECM), and 3) a stalled or decreased rate of epithelialization.

In other embodiments, "wound healing" refers to one or more of the following: improving of tissue repair, faster or increasing rate of wound healing, less scaring in the resulting healed area, the wounded area possesses tissue strength that is closer to that of uninjured tissue, the wounded tissue attains some degree of functional recovery. In an exemplary embodiment, the increasing rate of wound healing by administering the composition described herein involves the increased migration or proliferation of epithelial cells by at least 1%, 5%, 10%, 20%, 30%, 40%, 50% compared to that of a subject without administering the composition described herein.

In some embodiments, the composition comprises a β-1 adrenergic receptor antagonist. In some embodiments, the composition is substantially free of β-2 adrenergic receptor antagonist or non-selective β adrenergic receptor antagonist. The composition may be administered in a pharmaceutically acceptable carrier.

The composition can be formulated for systemic (such as oral or intravenous), intradermal, subcutaneous, intramuscular or topical administration. In some embodiments, the composition is formulated to one of the following form for topical delivery: ointment, cream, solution, gel, suspension, spray or lotion. In other embodiments, the composition is formulated for slow or sustained release.

Non-limiting examples of the β-1 adrenergic receptor antagonist include atenolol, betaxolol, bisoprolol, esmolol, acebutolol, metoprolol, nebivolol, or a combination thereof.

In one embodiment, the method further comprises the step of administering at least one therapeutic agent useful for wound healing. Such therapeutic agents include but are not limited to growth factors, cytokines, chemokines, antibodies, inhibitors, antibiotics (with or without silver), immunosuppressive agents, steroids, zinc, hyperbaric oxygen, antifungals, anti-virals, other cell types (e.g., stem cells, bioengineered skin, skin substitutes, and skin equivalents) or debriding agents (for example, Collagenase SANTYL and cadexomer iodine). In certain embodiments, the therapeutic agent useful for wound healing may be used in combination.

When the β-1 adrenergic receptor antagonist composition is administered in combination or alternation with at least one therapeutic agent useful for wound healing, less β-1 adrenergic receptor antagonist composition, fewer administration time points and/or increased time interval may be needed to be therapeutically effective.

In addition, one of skill in the art may readily determine the appropriate dose and the number of doses of the β-1 adrenergic receptor antagonist to be administered for a particular type of wound, depending on, for example, severity and type of wound, patient age, weight, sex, comorbidity and other medications being administered to the patient. The skilled artisan will recognize that a preferred dose is one which produces a therapeutic effect, such as increased wound healing, in a patient in need thereof. In certain embodiments, one dose is administered once a day for a given number of days (i.e. for 7 days, for 1 month, etc.). In other embodiments, multiple doses may be administered in one day (every 2, 4, 6, or 12 hours, etc.). Multiple doses per day for multiple days is also contemplated by the invention.

Apparatus for Wound Healing or Treating a Wound

The present invention also provides an apparatus for wound healing or treating a wound, comprising (a) dressing and (b) a composition comprising an effective amount of β-1 adrenergic receptor antagonist.

The term "dressing" refers to a dressing for topical application to a wound. Non limiting examples of dressing include at least one layer of woven or nonwoven textile/fabric material (e.g., gauze, sponges, cellulose, cotton or rayon), foam such as polyurethane foam, hydrogel such as polyurethane hydrogel, hyaluronic acid hydrogel or polyacrylate hydrogel, gelatin, carboxymethyl cellulose, pectin, alginate, silicon, collagen, transparent films, fillers, biodegradable polymeric matrix, any suitable biocompatible material or a combination thereof.

The dressing can be impregnated with the composition described herein, or at least one surface of the dressing is coated with the composition described herein. The one embodiment, the apparatus further comprises an instruction for using the composition contained therein for wound healing.

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated. Some of the procedures are described below for illustrative purpose.

Example 1

A female patient with severe, relapsing paronychia and pyogenic granuloma-like lesion on her left thumb (induced by afatinib) has been treated with topical betamethasone valerate ointment, gentamicin sulfate cream and 10% aqueous silver nitrate previously without any improvement (FIG. 1, A).

Figure 1B:
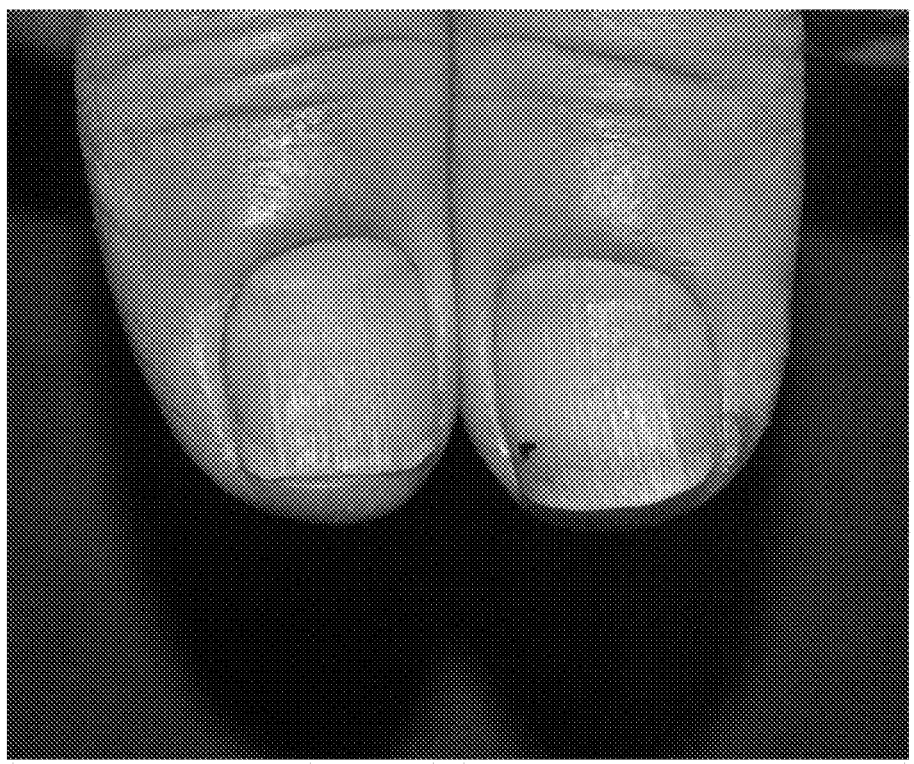

She was subsequently treated with topical 0.25% betaxolol drops once daily (Alcon Laboratories, USA) for 4 weeks under occlusion. FIG. 1B shows the complete resolution of paronychia and pyogenic granuloma-like lesion after 4 weeks of daily 0.25% betaxolol drop treatment.

Example 2

Figure 2A:
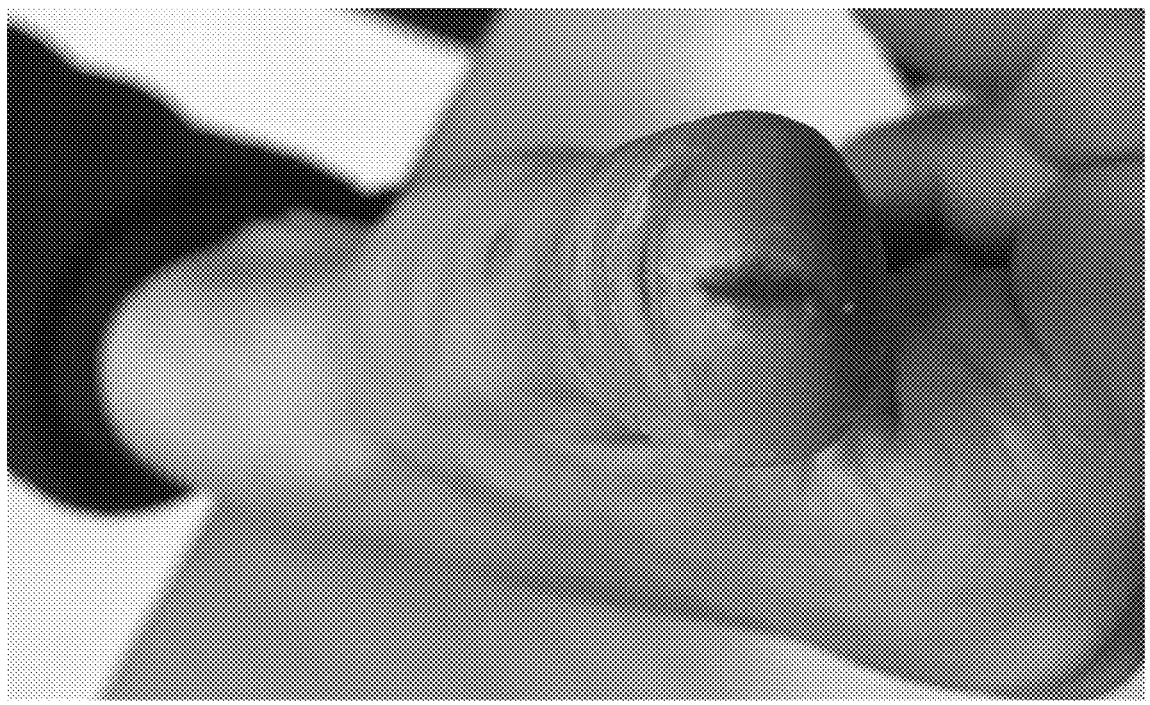
FIG. 2A and FIG. 2B are photo images of a patient with deep figures of the right thumb before (FIG. 3A) and after 4 weeks of topical betaxolol treatment (FIG. 3B).
Figure 2B:

10 patients with deep fissure over palms or soles induced by EGFR inhibitors were treated with topical 0.25% betaxolol drops (Alcon Laboratories, USA) once a day. Deep fissure wound healed within one week of treatment in all of the 10 patients, see FIG. 2A and FIG. 2B.

The results show 0.25% Betaxolol drop is an effective treatment for deep fissures.

Example 3

An in vivo study was performed to examine the effectiveness of a non-selective β blocker and a β1-blocker using rats. The rats were divided into 3 groups: (a) control (n=2); (b) non-selective β blocker (n=1); and (c) β1-blocker (n=1). On Day 0 of the experiment, 3 back incisions were made on each rat. The size of the back incisions are 1.5 cm×1.5 cm, 1 cm×1 cm and 0.5 cm×0.5 cm for the top, middle and bottom incisions as shown on FIG. 4A.

The rats in the control group received no treatment, the rat in the non-selective β blocker group received 0.5% Timoptol drop (MSD, USA) twice a day (30 µl for the top incision, 13 µl for the middle incision and 3.3 µl for the bottom incision) and the rat in the β1-blocker group received 0.25% Betoptic drop (Alcon Laboratories, USA) twice a day (30 µl for the top incision, 13 µl for the middle incision and 3.3 µl for the bottom incision).

Figure 3A:
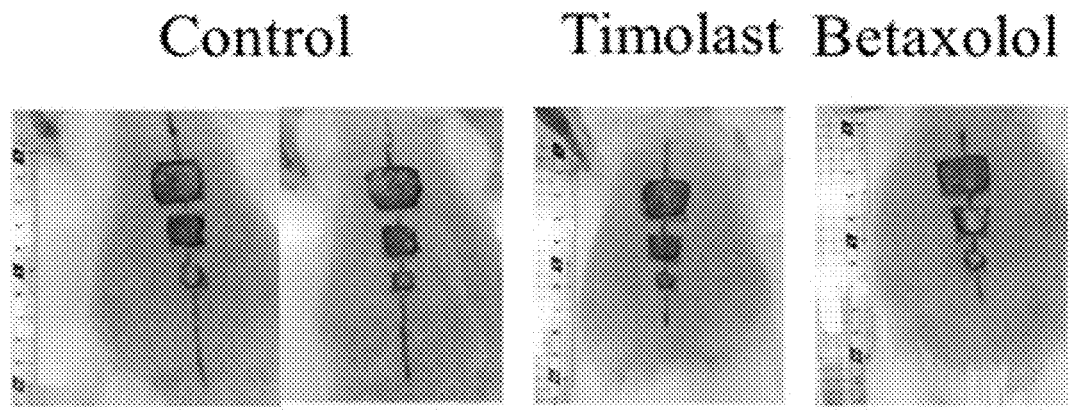
FIG. 3A to FIG. 3E are a series of photo images illustrating the effect of no treatment (control), timolast (non-selective β-adrenergic antagonist) and betaxolol (β 1-adrenergic antagonist) on back incisions of rats on day 0 (FIG. 3A), Day 1 (FIG. 3B), Day 4 (FIG. 3C), Day 7 (FIG. 3D) and Day 10 (FIG. 3E).
Figure 3B:
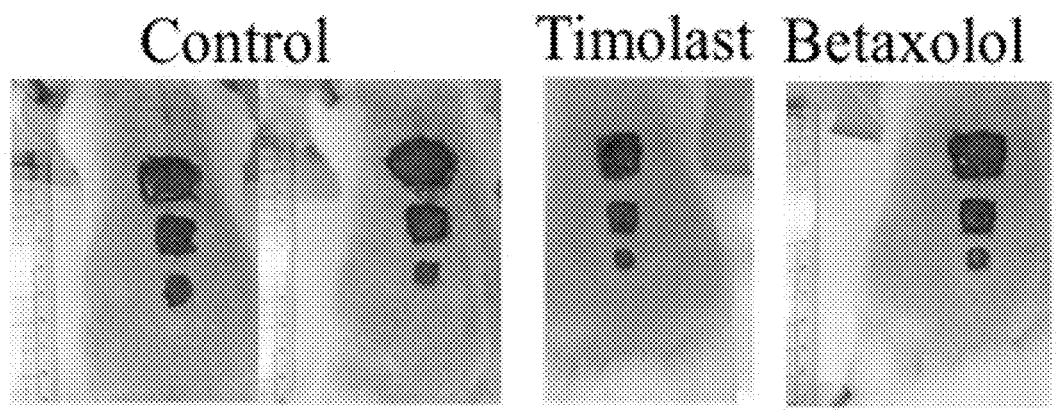
Figure 3C:
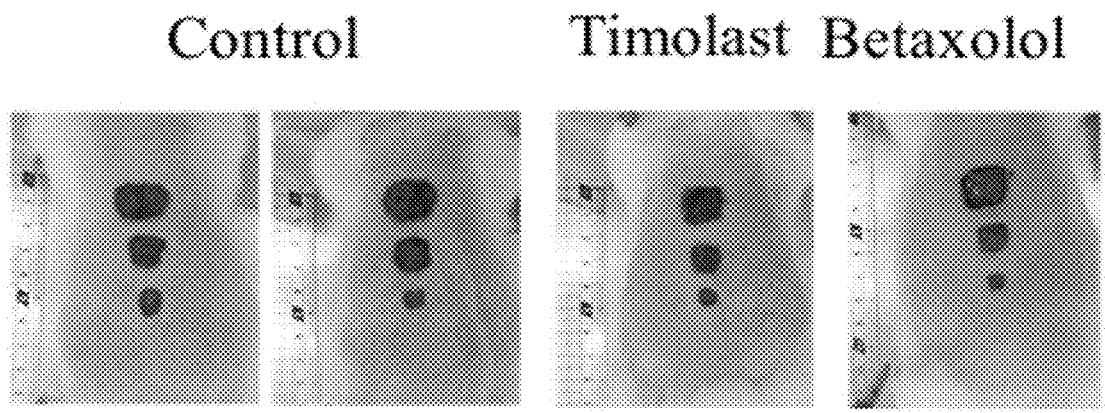
Figure 3D:
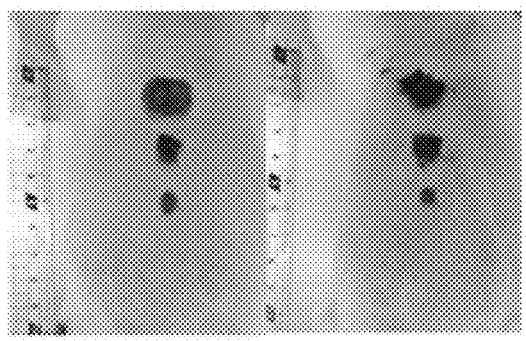
Figure 3D:
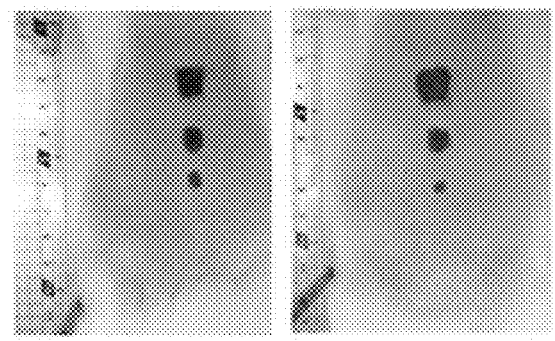
Figure 3E:
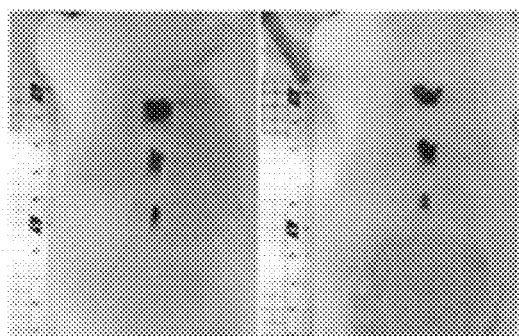
Figure 3E:
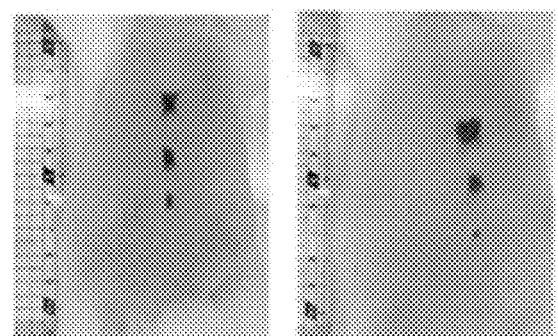

FIG. 3C to FIG. 3E show the back incisions treated with 0.25% Betoptic drop is less erythematous and smaller in size after 7 days of treatment compared to the back incisions treated with 0.5% Timoptol drops and no treatment. The results indicate Betoptic (betaxolol) is more effective to promote wound healing.

Figure 4A:
FIG. 4A to FIG. 4C are a series of microscopic images showing the back wound of rats without any treatment (FIG. 4A), or treated with 10 days of timolast (FIG. 4B) or betaxolol (FIG. 4C).
Figure 4B:
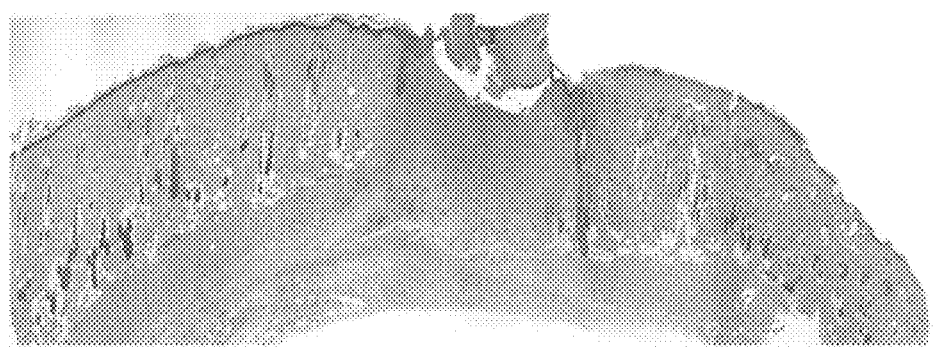
Figure 4C:
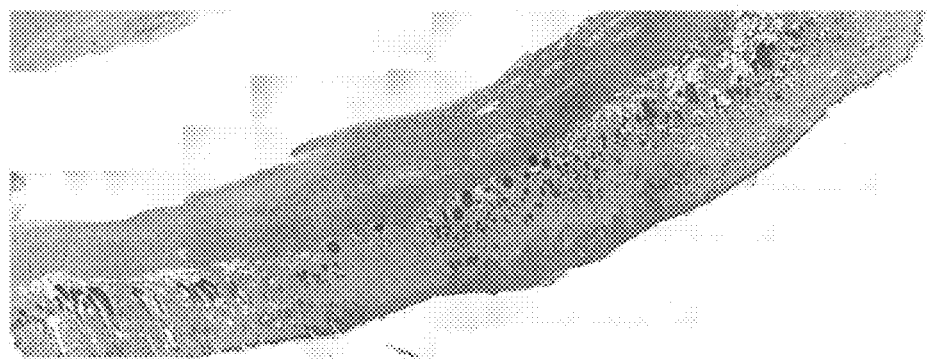

FIG. 4A to FIG. 4C shows microscopic changes of the 1 cm×1 cm back wounds of the 3 groups of rats on Day 10. The back incision treated with 10-day of 0.25% betaxolol drop was almost completely healed with re-growth of fibroblasts, complete re-epithelization of epidermis, and no evidence of debri (FIG. 4C). The back incision treated with 10-day of 0.5% Timoptol drop shows incompletely healing, characterized with incomplete re-epithelization of the epidermis, less fibroblast activity and evidence of debri.

What is claimed is:

1. A method for treating a wound in a patient comprising the step of administering a composition comprising an effective amount of a β-1 adrenergic receptor antagonist to the patient in need thereof, wherein the wound is paronychia.

2. The method of claim 1, wherein said wound is paronychia induced by targeted therapy.

3. The method of claim 1, wherein the β-1 adrenergic receptor antagonist is selected from the group consisting of atenolol, betaxolol, bisoprolol, esmolol, acebutolol, metoprolol, and nebivolol and a combination thereof.

4. The method of claim 1, further comprising administering an additional therapeutic agent for wound healing.

5. The method of claim 4, wherein the additional therapeutic agent for wound healing is selected from the group consisting of growth factors, cytokines, chemokines, antibodies, antibiotics, immunosuppressive agents, steroids, zinc, hyperbaric oxygen, anti-fungal agents, anti-viral agents, stem cells, bioengineered skin, debriding agents, and a combination thereof.

6. The method of claim 2, wherein the β-1 adrenergic receptor antagonist is selected from the group consisting of atenolol, betaxolol, bisoprolol, esmolol, acebutolol, metoprolol, and nebivolol and a combination thereof.

* * * * *